United States Patent
Maeda (10) Patent No.: US 8,632,667 B2
(45) Date of Patent: Jan. 21, 2014

(54) DETERIORATION SIGNAL GENERATION DEVICE FOR OXYGEN SENSOR

(75) Inventor: Seiji Maeda, Inazawa (JP)

(73) Assignee: NGK Spark Plug Co., Ltd., Aichi (JP)

( * ) Notice: Subject to any disclaimer, the term of this patent is extended or adjusted under 35 U.S.C. 154(b) by 241 days.

(21) Appl. No.: 13/009,261

(22) Filed: Jan. 19, 2011

(65) Prior Publication Data
US 2011/0174615 A1    Jul. 21, 2011

(30) Foreign Application Priority Data

Jan. 20, 2010 (JP) .................................. 2010-010429

(51) Int. Cl.
*G01N 27/419* (2006.01)
(52) U.S. Cl.
USPC ......... 204/424; 73/23.31; 73/23.32; 204/425; 204/426; 204/427; 204/428
(58) Field of Classification Search
USPC ..................... 204/424–429; 73/23.31–23.32
See application file for complete search history.

(56) References Cited

U.S. PATENT DOCUMENTS

| 7,499,789 B2 * | 3/2009 | Toda et al. ..................... 701/109 |
| 2009/0229343 A1 * | 9/2009 | Ishiguro et al. .............. 73/23.31 |

FOREIGN PATENT DOCUMENTS

JP    2004-093957 A    3/2004

\* cited by examiner

*Primary Examiner* — Bach Dinh
(74) *Attorney, Agent, or Firm* — Sughrue Mion, PLLC (57) ABSTRACT

A deterioration signal generation device for an oxygen sensor having a power supply different than a power supply connected to an external device, including a connection unit for electrically connecting the ground lines of the respective power supplies; a first acquisition unit for electrically connecting to a first output line at a reference potential side and to a second output line at a sensor potential side of the oxygen sensor, to obtain first and second potentials, respectively; an operation unit that calculates a first differential value between the first and second potentials; a processing unit that performs an operation on the first differential value; a second acquisition unit that acquires a third potential of a first input line at a reference potential side of the external device; and an output unit that generates the deterioration signal by superposing the second differential value on the third potential.

2 Claims, 4 Drawing Sheets

FIG. 5 ued States Patent

DETERIORATION SIGNAL GENERATION DEVICE FOR OXYGEN SENSOR

BACKGROUND OF THE INVENTION

1. Field of the Invention

The present invention relates to a deterioration signal generation device for an oxygen sensor which generates, from a detection signal of an oxygen sensor, a pseudo output value (degeneration output signal) simulating a deteriorated sate of the oxygen sensor, the oxygen sensor outputting a detection signal based on the concentration of oxygen in exhaust gas of an internal combustion engine.

2. Description of the Related Art

A related art oxygen sensor is known which is mounted in an exhaust passage of an internal combustion engine, such as a vehicle engine, to check whether the air-fuel ratio is rich or lean based on the concentration of oxygen in the exhaust gas. A detection signal output from the oxygen sensor is transmitted to an ECU (Electronic Control Unit) performing various engine controls, and the ECU executes feedback control of the air-fuel ratio such as by adjusting the fuel injection amount in the engine based on the detection signal thus received.

Since such oxygen sensors may slightly deteriorate due to aging upon use and exposure to exhaust gas in an exhaust gas passage over a long period of time, programs or devices are incorporated into the ECU for detecting deterioration of the oxygen sensor. While an actual vehicle is tested to check the operation of a program, etc., for detecting deterioration of the oxygen sensor, deterioration signal generation devices (deterioration simulators) capable of generating a pseudo deterioration signal simulating a deteriorated state of the oxygen sensor have been developed (see for example, Patent Document 1). For example, the deterioration signal generation device of Patent Document 1 is disposed between a normal oxygen sensor (reference sensor) mounted on a target vehicle to be tested and an ECU. The device processes a detection signal input from the reference sensor to generate a pseudo deterioration signal and outputs the deterioration signal to the ECU.

[Patent Document 1] JP-A 2004-93957

3. Problems to be Solved by the Invention

Since an ECU, however, is designed according to different standards for individual manufacturers, or vehicle models, reference potentials as a reference of the operational potential of the ECU itself may vary. Since a reference potential of an oxygen sensor connected to the ECU is subject to a reference potential of the ECU, a detection signal output from the oxygen sensor to the ECU is also subject to the reference potential of the ECU. Accordingly, increased testing accuracy has been required for each of deterioration signal generation devices outputting an appropriate signal level based on a reference potential of the ECU of individual manufacturers, or vehicle models.

In addition, the ECU is generally supplied with electric power from a vehicle battery, but arrangement of the battery and ECU of the vehicle is fixed and the wiring resistance in an electric power supply line may easily increase. In contrast, the deterioration signal generation device is readily arranged such that the wiring resistance in the electric power supply line may be relatively low as compared with that of the ECU, even though electric power is supplied from a battery or an external power supply. The reference potential of the deterioration signal generation device is adjusted to equal the reference potential of the ECU. However, for example, although each of the reference potentials is connected to ground, it is difficult to make each of the reference potentials exactly equal whenever the test is performed due to an effect such as wiring resistance.

SUMMARY OF THE INVENTION

The invention has been made to solve the above problems. It is therefore an object of the invention to provide a deterioration signal generation device for an oxygen sensor capable of generating a deterioration signal by acquiring a detection signal with high accuracy, and without depending on operational circumstances upon connecting an external apparatus and establishing a common ground.

According to a first aspect, the present invention provides a deterioration signal generation device for generating a deterioration signal simulating a deteriorated state of an oxygen sensor from a detection signal of the oxygen sensor, the oxygen sensor outputting a detection signal which abruptly changes in signal value around a specific air-fuel ratio in response to the concentration of oxygen in an exhaust gas of an internal combustion engine, the deterioration signal generation device outputting the deterioration signal to an external device, and the deterioration signal generation device being supplied with electric power from a power supply different than a power supply connected to the external device, the deterioration signal generation device comprising: a connection unit for electrically connecting a ground line of a first power supply supplying electric power to the external device and a ground line of a second power supply supplying electric power to the deterioration signal generation device; a first acquisition unit for electrically connecting the deterioration signal generation device to a first output line at a reference potential side of the oxygen sensor and to a second output line at a sensor potential side of the oxygen sensor that changes in potential in response to oxygen concentration, and that acquires a first potential of the first output line and a second potential of the second output line; an operation unit that calculates a first differential value between the first potential and the second potential; a processing unit that performs one or more operations on the first differential value in response to a target deterioration state to thereby obtain a second differential value; a second acquisition unit that acquires a third potential of a first input line at a reference potential side of the external device, which first input line would be connected to the first output line in a case where the oxygen sensor is connected to the external device; and an output unit that generates the deterioration signal having as a signal value a fourth potential obtained by superposing the second differential value on the third potential, to thereby output the deterioration signal to a second input line at a sensor potential side of the external device, which second input line would be connected to the second output line in a case where the oxygen sensor is connected to the external device.

In the first aspect, even though each of an external apparatus and a deterioration signal generation device are connected to different power supplies, a reference potential of an external apparatus and a reference potential of a deterioration signal generation device may be made nearly equal by electrically connecting the ground line of a first power supply and the ground line of a second power supply. Accordingly, since a first potential as a potential reference of the reference sensor may be maintained nearly equal in both the case where a reference sensor (oxygen sensor) is connected to an external apparatus and in the case where a reference sensor (oxygen sensor) is connected to a deterioration signal generation device, the value of a detection signal acquired by the deterioration signal generation apparatus may originally be equal to the value of a detection signal acquired by the external apparatus. In addition, since a first differential value is calculated and processed by acquiring a first potential and a second potential of the reference sensor, this process is independent of a reference potential. Accordingly, a process with a high degree of accuracy may be performed without affecting the first differential value even though the reference potential of the deterioration signal generation device may change. Further, the deterioration signal has a high degree of accuracy without depending on a reference potential of the deterioration signal generation device, by generating a deterioration signal having as a signal value a fourth potential which results from superposing the second differential value acquired by the process onto the third potential obtained from the external apparatus. In addition, even though a reference potential of the external apparatus is affected and changed by noise or offset due to a load connected to the first power supply, the third potential as a reference of the signal value of the deterioration signal likewise changes. Accordingly, the differential value between the third potential and the fourth potential, that is, a second differential value, is not affected, and thus the degree of accuracy is high.

According to a second aspect, the present invention provides a deterioration signal generation device for generating a deterioration signal simulating a deteriorated state of an oxygen sensor from a detection signal of an oxygen sensor, the oxygen sensor outputting a detection signal which abruptly changes in signal value around a specific air-fuel ratio in response to the concentration of oxygen in an exhaust gas of an internal combustion engine, and the deterioration signal generation device outputting the deterioration signal to an external device, the deteriorated signal generating device being supplied with electric power from a power supply commonly connected to the external device, the deterioration signal generation device comprising: a first acquisition unit for electrically connecting the deterioration signal generation device to a first output line at a reference potential side of oxygen sensor and to a second output line at a sensor potential side of the oxygen sensor that changes in potential in response to oxygen concentration, and that acquires a first potential of the first output line and a second potential of the second output line; an operation unit that calculates a first differential value between the first potential and the second potential; a processing unit that performs one or more operations on the first differential value in response to a target deterioration state to thereby process into a second differential value; a second acquisition unit that acquires a third potential of a first input line at a reference potential side of the external device, which first input line would be connected to the first output line in a case where the oxygen sensor is connected to the external device; and an output unit that generates the deterioration signal having as a signal value a fourth potential obtained by superposing the second differential value on the third potential, to thereby output the deterioration signal to a second input line at a sensor potential side of the external device, which second input line would be connected to the second output line in a case where the oxygen sensor is connected to the external device.

In the second aspect of the invention, an external apparatus and a deterioration signal generation device are connected to the same power supply, such that a reference potential of the external apparatus and a reference potential of the deterioration signal generation device become nearly equal. Accordingly, since a first potential as a potential reference of the reference sensor may be maintained in a nearly equal state in both the case where a reference sensor (oxygen sensor) is connected to an external apparatus and in the case where a reference sensor (oxygen sensor) is connected to a deterioration signal generation device, the signal value of a detection signal acquired by the deterioration signal generation device may originally be equal to the signal value of detection signal acquired by the external apparatus. In addition, since a first differential value is calculated and processed by acquiring a first potential and a second potential of the sensor, this process is independent of a reference potential. Accordingly, a process with a high degree of accuracy may be performed without affecting the first differential value even though the reference potential of the deterioration signal generation device may change. Further, the deterioration signal has a high degree of accuracy even without depending on a reference potential of the deterioration signal generation device, by generating a deterioration signal having as a signal value a fourth potential which results from superposing the second differential acquired by the process onto the third potential obtained from the external device. In addition, even though a reference potential of the external apparatus is affected and changed by noise or offset due to a load connected to the first power supply, the third potential as a reference of the signal value of the deterioration signal likewise changes. Accordingly, the differential value between the third potential and the fourth potential, that is, a second differential value, is not affected, and thus the degree of accuracy is high.

In a preferred embodiment of the first or second aspects, the processing unit performs, according to a deterioration state (deterioration mode) of the oxygen sensor that a user using the deterioration signal generation device of the invention requires (intentionally sets), at least one operation that simulates a predetermined deterioration state selected from the group consisting of: a gain operation for changing gain of a signal value of the detection signal, an offset operation for changing a signal value of the detection signal up or down by a fixed amount; a timing characteristics operation for delaying response of the detection signal to a change in concentration of a specific component (e.g., oxygen) in a target gas to be measured, and a response characteristics operation for changing a rate of change (time constant delay) of the detection signal in response to a change in concentration of a specific component in a target gas to be measured, to thereby process the first differential value into the second differential value. Since one or more of the gain operation, offset operation, timing characteristics operation and response characteristics operation are performed, thereby simulating various deterioration states of the oxygen sensor, various tests or developments may be performed more definitely, more accurately and more easily. In addition, various operations such as gain operation, etc., may separately produce deterioration signals representing states that are different from each other, in cases where the air-fuel ratio changes from a lean side to a rich side and from a rich side to a lean side on the basis of a specific air-fuel ratio (e.g., theoretical fuel-air ratio) as a boundary.

BRIEF DESCRIPTION OF THE DRAWINGS

Illustrative aspects of the invention will be described in detail with reference to the following figures wherein.

DETAILED DESCRIPTION OF THE PREFERRED EMBODIMENTS

The invention will now be described in detail with reference to the drawings. However, the present invention should not be construed as being limited thereto.

First Illustrative Embodiment

Hereinafter, a deterioration signal generation device for an oxygen sensor according to a first illustrative embodiment of the invention will be described in brief. The oxygen sensor of the invention includes, for instance, an oxygen sensor (a so called 2 type oxygen sensor) outputting a detection signal whose output value abruptly changes on the basis of a specific air-fuel ratio (a theoretical fuel-air ratio in the first illustrative embodiment) as a boundary and in response to the concentration of oxygen in an exhaust gas. The sensor simulator 1 is connected to an oxygen sensor 3, which is in a normal state (not deteriorated), and identical in configuration to the target oxygen sensor of product for which a deteriorated state is simulated.

Meanwhile, a detailed illustration of the configuration of the oxygen sensor is omitted because a conventional oxygen sensor can be used as the oxygen sensor in the invention. Hereinafter, a detection principle of the air-fuel ratio (the concentration of oxygen in an exhaust gas) of an exhaust gas by a sensor element employed in an oxygen sensor, however, will be described briefly. The sensor element has a cup shape or a plate shape in which a solid electrolyte, which is made of zirconium having oxygen-ion conductivity above an active temperature, is sandwiched between a pair of porous electrodes. The oxygen sensor (sensor device) detects the concentration of oxygen based on the principle that oxygen ions move in the solid electrolyte to thereby produce an electromotive force (detection signal) when there is a difference in oxygen partial pressure between the atmospheres contacting opposing sides (one side is formed with an exhaust gas atmosphere and the other side is formed with a reference gas atmosphere) of the solid electrolyte.

The signal value of the detection signal indicates a potential difference between the electrode of the one side (OZ(−) electrode) and the electrode of the other side (OZ(+) electrode), based on the potential of the one side porous electrode (OZ(−) electrode). The signal value sharply (abruptly) changes between the rich side and the lean side at a point where the air-fuel ratio of exhaust gas corresponds to a theoretical air-fuel ratio. Generally, in the case where the air-fuel ratio of exhaust gas is on the rich side (in the case where the concentration of oxygen in an exhaust gas is lower than the concentration of oxygen of a theoretical air-fuel ratio), the signal value (potential difference) of the detection signal represents approximately 0.9 V. In the case of the lean side (the case where the concentration of oxygen in an exhaust gas is greater than the concentration of oxygen of a theoretical air-fuel ratio), the signal value represents approximately 0.05 V. As an example of such an oxygen sensor, the embodiment of the invention may employ the oxygen sensor disclosed in JP Patent publication No. 2004-138599-A, incorporated herein by reference. The oxygen sensor has a form in which a heater is interposed within a cup-shaped sensor element, a front end of the sensor element is surrounded by a protector having gas-flow holes, and the sensor element is held within a housing. The oxygen sensor has a connector for connecting with an external apparatus (ECU 3 which will be described below), and the connector is electrically connected to the OZ(−) electrode of sensor device and the OZ(+) of oxygen device through a lead line and a terminal electrode.

Figure 1:
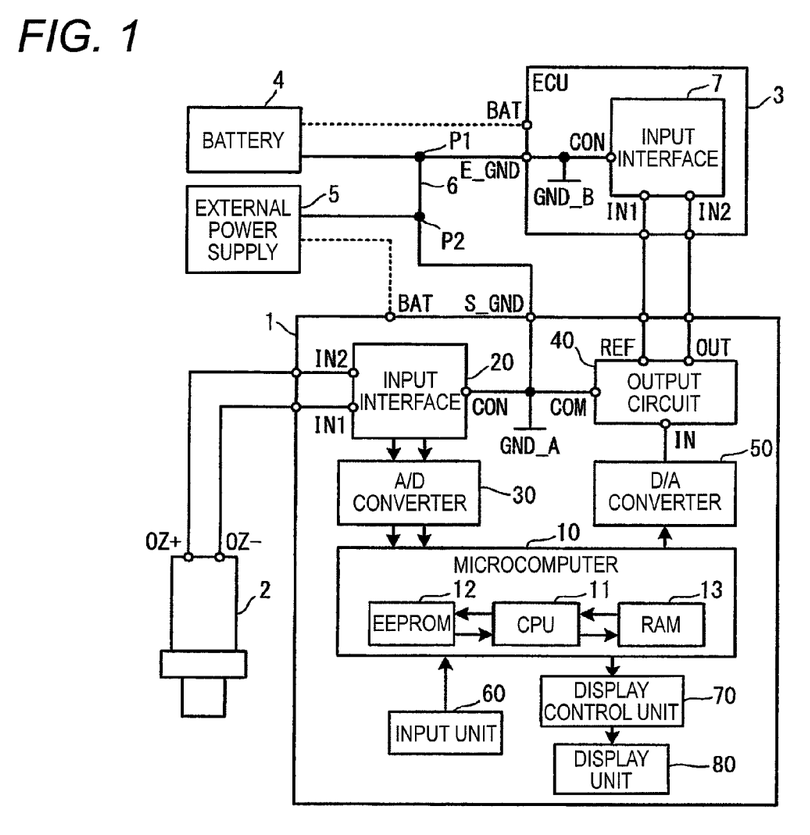
FIG. 1 is a block diagram showing a schematic configuration of a sensor simulator according to the first illustrative embodiment of the invention.

As shown in FIG. 1, the sensor simulator 1 is arranged between a reference sensor 2 as an oxygen sensor which is mounted in an exhaust passage (not shown) of a vehicle and an electronic control unit (ECU) 3 for electronically controlling a vehicle. The sensor simulator 1 includes a receptacle connected to a connector of the reference sensor 2 and a connector connected to the ECU 3 instead of the reference sensor 2. The reference sensor 2 outputs a detection signal in response to the concentration of oxygen in an exhaust gas flowing within the exhaust passage, and the detection signal is input to the sensor simulator 1. The sensor simulator 1 processes the signal value of the inputted detection signal by performing a processing program, described below, in a microcomputer 10, generates a deterioration signal through an output circuit, described below, and outputs it to the ECU 3. The ECU 3 controls an engine which is not shown (for example, injection timing control, or control of an injection amount of fuel being injected from an injector, or ignition timing control), in response to the inputted deterioration signal. In addition, the ECU 3 supplies a heater driving voltage to a heater circuit (not shown) of the reference sensor 2, and instructs the earlier activation of a sensor element (not shown), or the stabilization of a sensor device even after activation.

The sensor simulator 1 includes a microcomputer 10 having a CPU 11 controlling itself, an EEPROM 12 being stored with processing programs, etc., and which is rewritable, and a RAM 13 temporarily storing various kinds of data, within a casing not shown. Meanwhile, the CPU 11, EEPROM 12 and RAM 13 of the microcomputer 10 are formed with a conventional configuration.

The microcomputer 10 is connected to an input interface 20 through an A/D converter 30. The analog detection signal, which is input from the reference sensor 2 through the input interface 20, is converted to a digital signal by the A/D converter 30, and input to the microcomputer 10. In more detail, the reference sensor 2 has a connector formed with an OZ(−) port and an OZ(+) port for acquiring the potential of the OZ(−) and OZ(+) electrodes of the sensor element. The OZ(−) and OZ(+) ports of the reference sensor 2 are connected to an IN 2 port and an IN 1 port of the input interface 20 of the sensor simulator 1, respectively. Meanwhile, the input interface 20 corresponds to a "first acquisition unit" of the invention. In addition, the OZ(−) port and OZ(+) port correspond to a "first output line" and a "second output line" of the invention, respectively.

In addition, the input interface 20 includes a CON port, and the CON port is connected to a reference potential GND_A of the sensor simulator 1. The input interface 20 acquires a potential of the OZ(−) port and the OZ(+) port of the reference sensor 2, and outputs the same to the A/D converter 30, respectively, relative to a reference potential GND_A connected through the CON port. The A/D converter 30 converts a potential of the OZ(−) port and the OZ(+) port from an analog to a digital quantity, and inputs to the microcomputer 10.

The microcomputer 10 is also connected to a D/A converter 50. The D/A converter 50 is connected to an output circuit 40. The D/A converter 50 performs a digital to analog conversion. This is because the signal values of the detection signal processed in the microcomputer 10 are output to the output circuit 40 formed with an electric circuit configured to perform analog processing.

Figure 2:
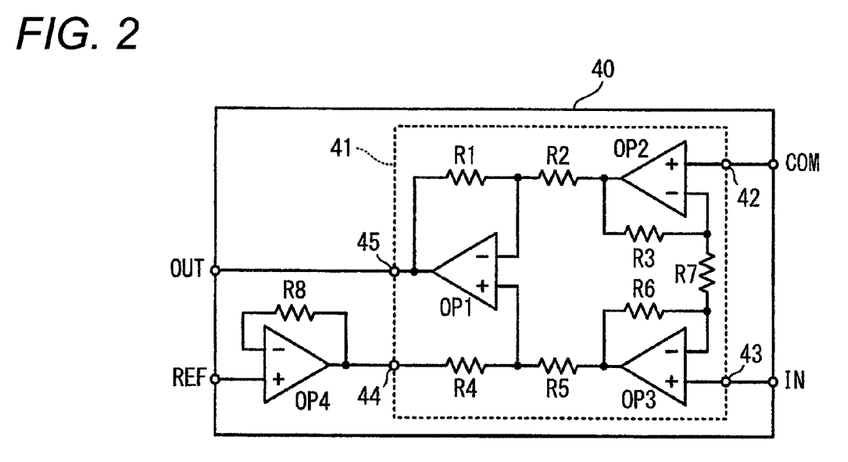
FIG. 2 is a view showing a schematic configuration of an electric circuit of the output circuit 40.

The output circuit 40 includes an analog circuit formed by the combination of a plurality of operational amplifiers and resistance elements. The detailed configuration of the output circuit 40 as an example is shown in FIG. 2. As shown in FIG. 2, the output circuit 40 includes, for instance, four operational amplifiers OP1, OP2, OP3 and OP4, and eight resistance elements R1, R2, R3, R4, R5, R6, R7 and R8. Among them, the operational amplifiers OP1, OP2 and OP3 and resistance elements R1, R2, R3, R4, R5, R6 and R7 form an instrumentation amplifier 41. Non-inverting input terminals of the operational amplifiers OP2, OP3 are connected to input terminals 42, 43 of the instrumentation amplifier, respectively. Inverting input terminals of the operational amplifiers OP2, OP3 are connected to output terminals of the same through the resistance elements R3, R6, respectively, and are also connected to each of the inverting input terminals through the resistance element R7. An output terminal of the operational amplifier OP2 is connected to an inverting input terminal of the operational amplifier OP1 through the resistance element R2, and is also connected to an output terminal of the operational amplifier OP1 corresponding to the output terminal 45 of the instrumentation amplifier 41 through the resistance element R1. Meanwhile, the output terminal of the operational amplifier OP3 is connected to a non-inverting input terminal of the operational amplifier OP1 through the resistance element R5, and is also connected to an input terminal 44 of the instrumentation amplifier 41 through the resistance element R4. The instrumentation amplifier 41 corresponds to the "output unit" of the invention.

Additionally, each of the terminals of the instrumentation amplifier 41 is connected to four input/output ports (IN port, COM port, OUT port, REF port) of the output circuit 40, respectively. In more detail, the input terminal 42 and the input terminal 43 each are connected to the COM port and IN port, and the output terminal 45 is connected to the OUT port. In addition, the input terminal 44 is connected to an output terminal of the operational amplifier OP4, and is also connected to an inverting input terminal of the operational amplifier OP4 through the resistance element R8. A non-inverting input terminal of the operational amplifier OP4 is connected to the REF port. As shown in FIG. 1, the COM port of the output circuit 40 is connected to the reference potential GND_A of the sensor simulator 1, and the IN port is connected to the microcomputer 10 through the D/A converter 50, as described above. The OUT and REF ports of the output circuit 40 are connected to the IN1 port and IN2 port of the input interface 7 of the ECU 3, respectively. Meanwhile, the IN1 port and IN2 port of the input interface 7 correspond to the "first input line" and the "second input line" of the invention, respectively.

As described below, the output voltage value of the deterioration signal generated in the microcomputer 10 is based on the reference potential GND_A of the sensor simulator 1 as a reference potential. As shown in FIG. 2, in the output circuit 40, the differential between the output voltage value of the deterioration signal input to the IN port by the operational amplifiers OP2, OP3 and the reference potential GND_A input to the COM port is input to the operational amplifier OP1. In addition, a potential of the IN1 port of the input interface 7 of the ECU 3 is input to the operational amplifier OP1 from the REF port. The operational amplifier OP1 superposes a potential GND_B difference between the output voltage value of the deterioration signal and the reference potential GND_A onto the potential at the IN1 port of the input interface 7 of the ECU 3, thereby outputting the difference as a deterioration signal from the OUT port to the IN2 port of the input interface 7. That is, the deterioration signal, as a reference signal based on the reference potential GND_B, is input to the ECU 3 by the output circuit 40. Meanwhile, the operational amplifier OP4 corresponds to the "second acquisition unit" of the invention.

Next, as shown in FIG. 1, the microcomputer 10 is additionally connected to an input unit 60 and a display controller 70. The input unit 60 is designed to allow a user of the simulator 1 to input set points, etc. (gain factor Gain, voltage value Offset, set point of lag time T, etc.) which are used in a processing program, to the same. The input unit 60 is employed with, for instance, a push switch, or a rotary switch. Meanwhile, the set points as inputted are stored in the EEPROM 12, and the previously inputted set points are maintained even though they are reused after electric power to the sensor simulator 1 is cut off. The display controller 70 serves to control the display of a display unit 80 displaying the inputted set points so that a user may check them. The display unit 80 is employed with an LCD display, for instance.

Although not shown, the sensor simulator 1 is also provided with a power supply circuit, etc., and a BAT terminal of the sensor simulator 1 is connected to a line (shown as dotted line) at an output side of an external power supply 5, thereby being supplied with electric power from the external power supply 5. A ground wire of the external power supply 5 is connected to the reference potential GND_A of the sensor simulator 1 through the S_GND terminal.

The ECU 3 has the same input interface 7 as the input interface 20 of the sensor simulator 1. The input interface 7 has the IN1 port, IN2 port and CON port, and the IN1 port and IN2 port are connected to the REF port and OUT port of the output circuit 40, respectively, as described above. The CON port of the input interface 7 is connected to the reference potential GND_B of the ECU 3. The reference potential GND_B is connected to the ground wire of a vehicle battery 4 through the E_GND of the ECU 3. Further, the BAT terminal of the ECU 3 is connected to an output line (shown as dotted line) of the battery 4, thereby receiving electric power from the battery 4. Meanwhile, the ECU 3 corresponds to the "external apparatus" of the invention, and the battery 4 corresponds to the "first power supply".

The battery 4 supplies electric power to various devices (loads) in addition to the ECU 3. The ECU 3 is affected by operation of the loads, thereby causing noise or offset of potential in some cases. In addition, the ground wire of the battery 4, which is connected to the reference potential GND_B of the ECU 3, is connected to connection point P2 on the ground wire of the external power supply 5, which is connected to the reference potential GND_A of the sensor simulator 1 at the connection point P1 through the connection line 6. That is, the reference potential GND_B of the ECU 3 and the reference potential GND_A of the sensor simulator 1 are connected to the ground in common. Meanwhile, the connection line 6 corresponds to the "connection unit" of the invention.

According to the illustrative embodiment of the invention, the sensor simulator 1 is adapted to have a circuit for processing a potential of the IN1 port and IN2 port of the input interface 20 different from the potential of the CON port (i.e., the reference potential GND_A). Accordingly, the input interface 20 may obtain the potential of the OZ(−) port and the potential of the OZ(+) port of the reference sensor 2, on the basis of (i.e., relative to) the reference potential GND_A. In addition, as described above, the input interface 7 of the ECU 3 is the same as the input interface 20, and is adapted to have a circuit for processing a potential of the IN1 port and IN2 port of the input interface 7 different from the potential of the CON port (i.e., the reference potential GND_B). Since the ECU 3 and sensor simulator 1 are connected to a common ground, the reference potential GND_A of the sensor simulator 1 and the reference potential GND_B of the ECU 3 may slightly be different from each other due to a difference in, for instance, wire resistance, but are nearly equal to each other. Accordingly, in both the case where the input interface 7 of the ECU 3 is connected to the reference sensor 2 and the case where the input interface 20 of the sensor simulator 1 is connected to the reference sensor 2, the potential of the OZ(−) port may be maintained in a nearly equal state, and the signal value of the detection signal, which is acquired by the sensor simulator 1, may equal the signal value of the detection signal, which is acquired by the ECU 3.

According to the illustrative embodiment of the invention, the input interface 20 may obtain the potential of the OZ(−) port and OZ(+) port of the reference sensor 2, and output each of the potentials to the microcomputer 10 through the A/D converter 30. The microcomputer 10 does not process the potential of the OZ(+) port, but rather the potential difference between the OZ(−) port and OZ(+) port by performing a processing program, as described below. Therefore, even in the case where the reference potential GND_A of the sensor simulator 1 changes, the potential difference between the OZ(−) port and OZ(+) port is not affected. Thereby, the signal value of the detection signal may be processed with a high degree of accuracy.

The output circuit 40 may acquire the potential of the IN1 port of the input interface 7 of the ECU 3 from the REF port, and superpose the potential difference between the OZ(−) port and the OZ(+) port after processing onto the potential of the IN1 port, to thereby output to the IN2 port of the input interface 7 through the OUT port. As described above, because a common ground is used, the potential of the IN1 port of the input interface 7 setting up the reference potential GND_B as a standard may specifically be predetermined even though the reference potential GND_A is set up as a standard. Accordingly, even though some inconsistency between the reference potential GND_A and the reference potential GND_B may develop due to a difference in wire resistance, the signal value of the deterioration signal acquired by the ECU 3 does not depend on the reference potential GND_A. This is because the potential of the IN1 port based on the reference potential GND_B of the ECU 3 is set as a reference, and thereby is not affected by the inconsistency and has a high degree of accuracy.

In addition, as described above, in the case where noise or potential offset occurs in the reference potential GND_B of the ECU 3, the reference potential GND_B may vary due to the noise or offset if the reference potential GND_A of the sensor simulator 1 is set as a reference. However, the ECU 3 is driven on the basis of the reference potential GND_B as a reference. In the case where the potential of the IN1 port based on the reference potential GND_B of the ECU 3 is affected by noise or offset and changes accordingly, the signal value of the detection signal, which is superposed (added) onto the potential of the IN1 port and inputted to the IN2 port, also changes equally. In this manner, the potential difference between the IN1 port and IN2 port is not affected, and the degree of accuracy is high.

Next, the deterioration signal generation processes will be described. The deterioration signal is generated by processing the signal value (potential difference of the OZ(−) port and OZ(+) port) of the detection signal of the reference sensor 2 during the process of carrying out a processing program in the microcomputer 10 and superposing it onto the potential of the IN1 port of the ECU 3 in the output circuit 40. The processing program may perform any of a gain process, an offset process, a response delay process and a lag time delay process for the signal value of the detection signal. The detailed process methods of gain process, offset process, response delay process and lag time delay process are conventionally known and will be described briefly hereinafter. For the details of the gain process, response delay process and waste time delay process, reference may be made to JP Patent Publication No. 2007-315210-A, for instance, incorporated herein by reference. In addition, for details of the offset process, reference may be made to JP Patent Publication No. 2008-203152-A, incorporated herein by reference. Meanwhile, the gain process, offset process, response delay process and lag time delay process correspond to the "gain operation", "offset operation", "response characteristics operation" and "timing characteristics operation" of the invention, respectively.

Figure 3:
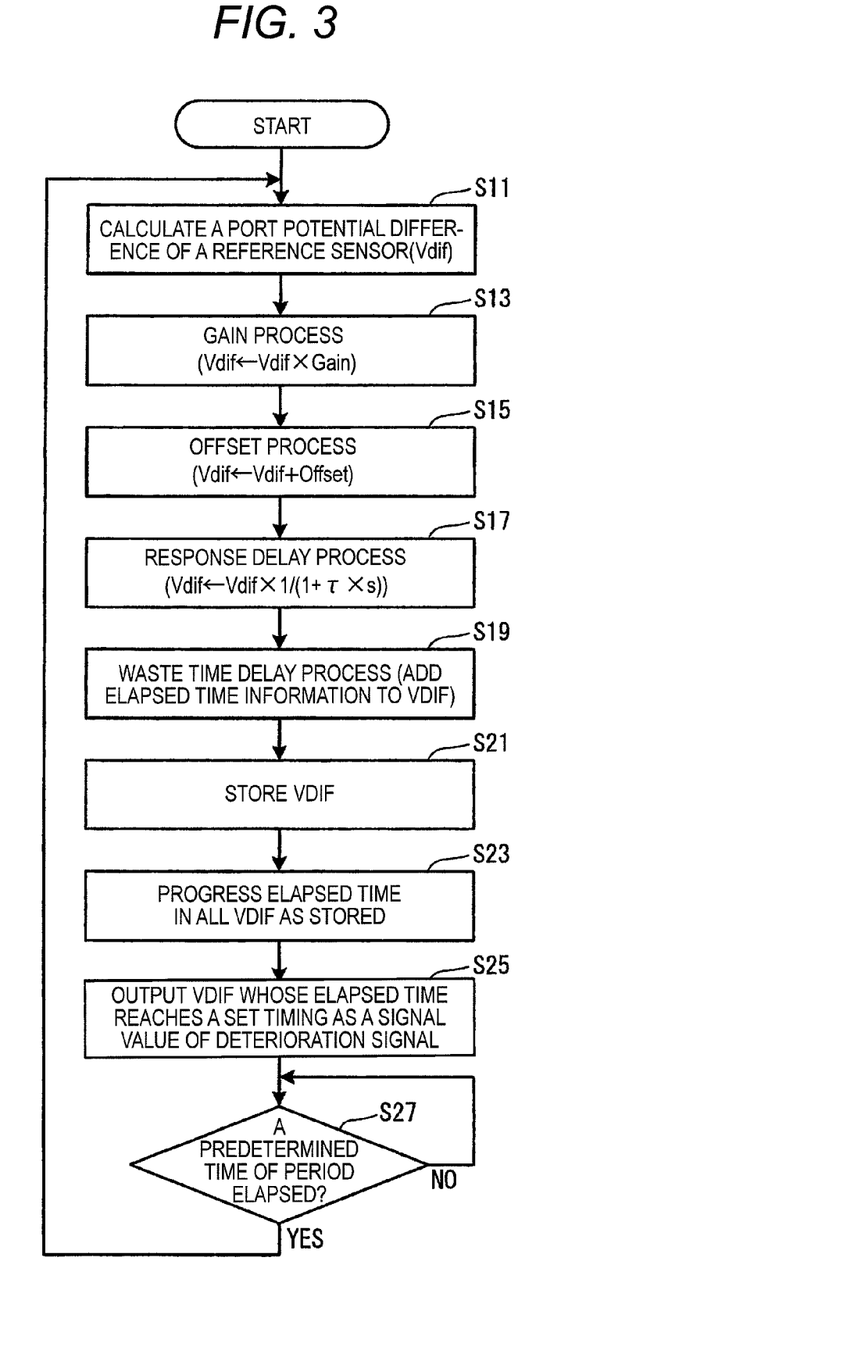
FIG. 3 is a flow chart of a process program.

The process for the signal value of the detection signal may be performed at predetermined timing intervals (e.g., every 1 msec) according to the processing program that is executed in the microcomputer 10. As shown in FIG. 3, the CPU 11 of the microcomputer 10 may read the voltage (voltage value) of the OZ(−) port and OZ(+) port of the reference sensor 2, which is inputted to from the input interface 20 through the A/D converter 30, thereby calculating a differential value. The differential value as calculated is stored in the RAM 13 as a variable Vdif (S11). In the step S11, the CPU 11, which performs an operation on the differential value (first differential value) in the voltage of the OZ(−) port and OZ(+) port of the reference sensor 2, corresponds to "operation unit" of the invention.

Figure 4:
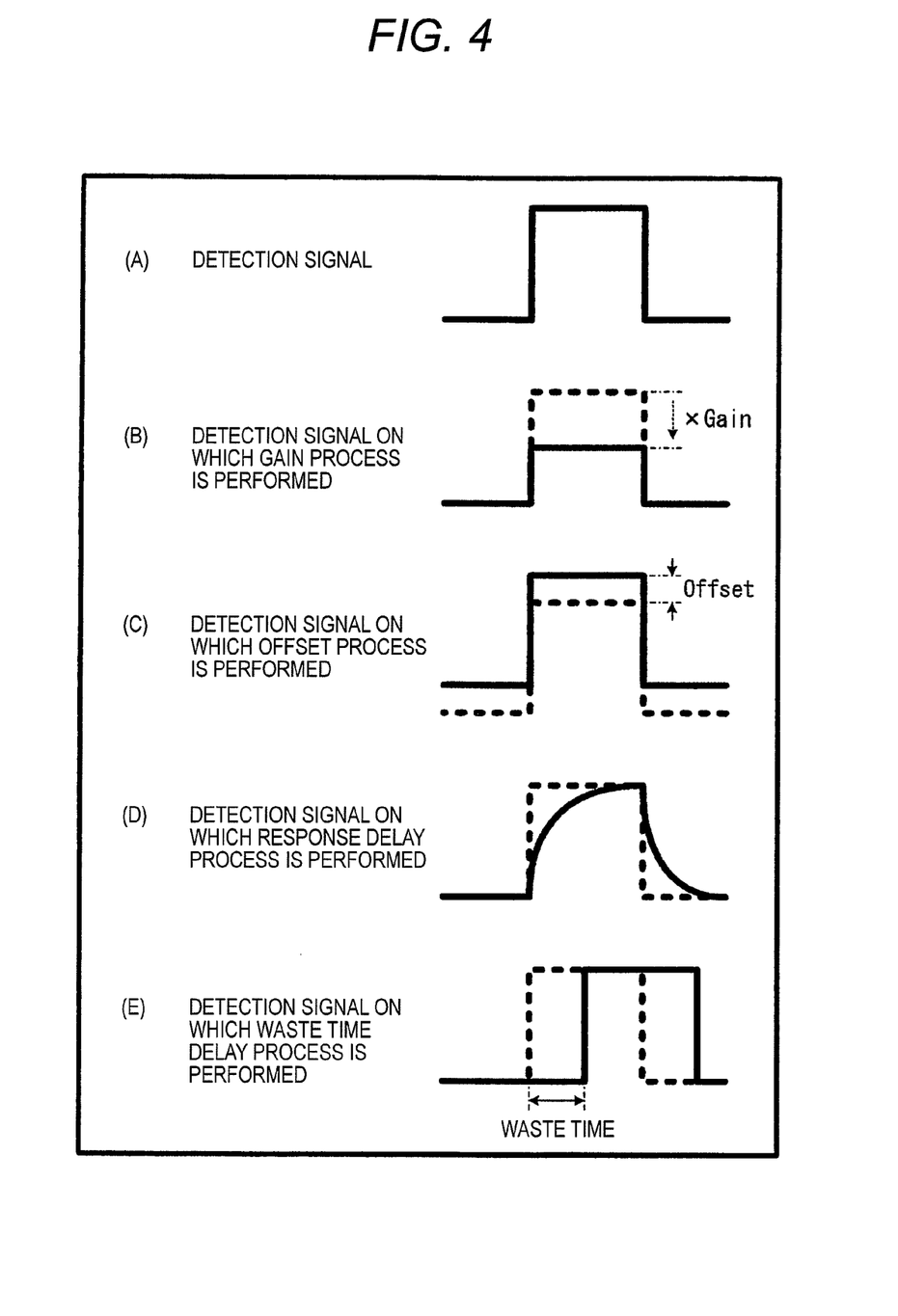
FIG. 4 is a view illustrating outlines of a gain process, an offset process, a response delay process, and a lag time delay process.

A gain processing (Vdif←Vdif×Gain), in which variable Vdif is multiplied by a predetermined gain factor Gain and the operational result is superposed onto the variable Vdif, is executed (S13). The gain processing is a process for multiplying the signal value of detection signal by a gain factor Gain, thereby amplifying or attenuating the value. For example, as shown in FIG. 4, if the gain processing (herein, attenuation) is executed for an original (reference) detection signal as shown in FIG. 4(A), the detection signal may be processed as a detection signal whose signal value is increased or decreased (herein, decreased), in response to the gain factor Gain, as shown in FIG. 4(B).

Next, regarding the variable Vdif, an offset processing (Vdif←Vdif+Offset), in which variable Vdif is superposed onto a predetermined voltage value Offset and the operational result is overwritten on the variable Vdif, is executed (S15). The offset processing is a process for changing the signal value of detection signal by a predetermined voltage value Offset. As shown in FIG. 4, for example, if the offset processing (herein, superposition of a plus voltage value Offset) is executed for an original (reference) detection signal as shown in FIG. 4(A), the signal value may be processed as a detection signal whose signal value is changed up or down (herein, changed upwardly), as shown in FIG. (C).

Next, regarding the variable Vdif, a response delay process (Vdif←Vdif×1/(1+τs)), in which an annealing is executed by performing an operation applying, for instance, a first delay transfer function and the operational result is rewritten on the variable, is executed (S17). The response delay process is a process for slowly changing (annealing) the signal value of detection signal. The first delay transfer function G(s) is as follows.

G(S)=k/(1+τs), wherein τ: time constant, k: gain (wherein provisionally predetermined as k=1)

For example, as shown in FIG. 4, if the response delay process is executed for an original (reference) detection signal as shown in FIG. 4(A), the signal value is slowly changed as compared with the original detection signal, thereby obtaining a detection signal delayed more than and following the original detection signal, as shown in FIG. 4(D).

In addition, the lag time delay process is executed as to the variable Vdif. The lag time delay process is a process for outputting a detection signal after time T that has been set up as a lag time. For example, as shown in FIG. 4, if the lag time delay process is executed for the original detection signal as shown in FIG. 4(A), a detection signal delayed in timing as compared with the original detection signal may be produced, as shown in FIG. 4(E).

The lag time delay process, as described above, serves to subsequently add an elapsed time information (first time, the elapsed time=0) to the current variable Vdif, which has been processed by the gain process, offset process and response delay process (S19), as stored in the RAM 13 (S21). Next, the elapsed time in all of the variables Vdif as stored progresses by a unit time (S23). Also, the variable Vdif whose elapsed time maintained as an elapsed time information reaches the waste time T is outputted as a signal value of the detection signal after processing to the output circuit (40) through the D/A converter 50 (S25). Meanwhile, the variable Vdif as obtained at this time and stored in the RAM 13 in step S21 is maintained in the RAM 13 until the lag time T lapses.

The processes in steps S11 to S25 each are performed with reference to the signal value of detection signal, thereafter waiting a lapse of predetermined time of a period (e.g., 1 msec) (S27: NO) and then returning to step S11 (S27: YES) to thereby perform processing of the signal value of detection signal as previously obtained. Meanwhile, the CPU 11, which performs operations on the signal value of the detection signal as processed in each of the steps S13 to S25, corresponds to the "processing means" of the invention.

Second Illustrative Embodiment

Figure 5:
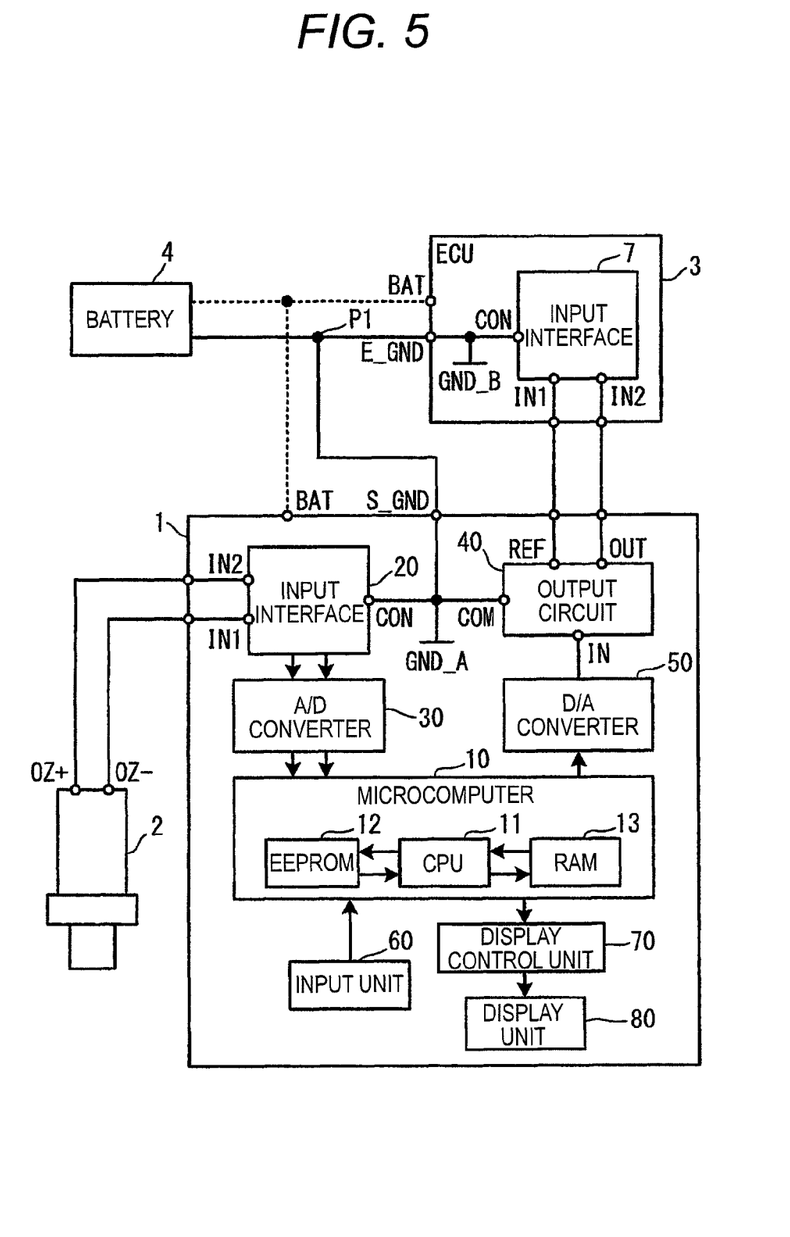
FIG. 5 is a block diagram showing a schematic configuration of the sensor simulator 1 according to a second illustrative embodiment of the invention.

Next, the deterioration signal generation device of an oxygen sensor according to a second illustrative embodiment will be described with reference to FIG. 5. According to the second illustrative embodiment of the invention, the electric power source of the sensor simulator 1 employs the same battery 4 as that of the ECU 3. As shown in FIG. 5, an output line (dotted line) of the battery 4 is connected to the BAT terminal of the sensor simulator 1, and likewise the ground line of the battery 4 is divided at the connection point P1 and connected to the reference potential GND_A of the sensor simulator 1 through the S_GND terminal. The reference sensor 2, ECU 3, and sensor simulator 1 are identical in configuration to those of the first illustrative embodiment. The reference potential GND_B of the ECU 3 and the reference potential GND_A of the sensor simulator 1 all are connected to the ground line of the battery 4, thereby realizing a common ground. That is, if the sensor simulator 1 is supplied with electric power from the battery 4, a common ground among the sensor simulator 1 and the ECU 3 is easily realized. The sensor simulator 1 is also operated in the same manner as in the first illustrative embodiment.

The invention is not limited to the illustrative embodiments described above, and various changes may be made within the spirit and scope of the claims appended hereto. For example, the output circuit 40 is configured by employing an instrumentation amplifier 41. However, the instrumentation amplifier need not be incorporated into the electric circuit. Instead, the electric circuit may be configured to superpose (add) a signal value of the detection signal as processed onto a reference potential of the ECU 3 by employing an amplifier.

In addition, as described above, the processing program was executed in the order of a gain process, an offset process, a response delay process and a lag time delay process. Alternatively, each of these processes may be executed independently, and any of the processes need not be executed. That is, one or more than one of these processes may be executed. In addition, the order of the processes may be changed arbitrarily. In the case where the degree in gain of the detection signal or response delay and lag time are changed, if each of the gain factor Gain for changing the gain, time constant τ of transfer function G(s) and lag time T may independently be set in the case of a change in the target air-fuel ratio from the rich side to the lean side or from the lean side to rich side, the sensor simulator 1 is preferably employed for developing a system capable of realizing an accurate air-fuel ratio feedback control.

In the present embodiment, the signal value of the detection signal is processed with software by performing the processing program, but it is possible to process the signal value with an analog or digital circuit having a logic circuit therein. In addition, an input/output interface such as a USB or RS232C may be provided and connected to a personal computer by employing a corresponding cable, to allow for input of set values or checking on a display, etc. In addition, the detection signal of the reference sensor 2 or the deterioration signal as generated may be output to a personal computer through an input/output interface such as a USB or RS232C to produce output waveforms on the personal computer that may be monitored. The output waveforms may also be displayed on the display unit 80. In addition, the invention is not limited to the oxygen sensor (reference sensor) 2 connected to the sensor simulator 1, having an output value sharply which abruptly changes just above or below a theoretical air-fuel ratio, but may be applied to a sensor in which an appropriate catalyst layer is formed on a measuring electrode (electrode exposed to an exhaust gas) provided in a solid electrolyte, and an output value which abruptly (sharply) changes just above or below an air-fuel ratio that has been shifted from a theoretical air-fuel ratio to a rich side or lean side by a predetermined value.

This application claims priority from Japanese Patent Application No. 2010-010429, filed on Jan. 20, 2010, the disclosure of which is incorporated herein by reference in its entirety.

What is claimed is:

1. A deterioration signal generation device for generating a deterioration signal simulating a deteriorated state of an oxygen sensor from a detection signal of the oxygen sensor, the oxygen sensor outputting a detection signal which abruptly changes in signal value around a specific air-fuel ratio in response to concentration of oxygen in an exhaust gas of an internal combustion engine, the deterioration signal generation device outputting the deterioration signal to an external device, and the deterioration signal generation device being supplied with electric power from a power supply different than a power supply connected to the external device, the deterioration signal generation device comprising:

a connector which electrically connects a ground line of a first power supply supplying electric power to the external device and a ground line of a second power supply supplying electric power to the deterioration signal generation device;

an interface which electrically connects the deterioration signal generation device to a first output line at a reference potential side of the oxygen sensor and to a second output line at a sensor potential side of the oxygen sensor that changes in potential in response to oxygen concentration, and that acquires a first potential of the first output line and a second potential of the second output line;

a calculator configured to calculate a first differential value between the first potential and the second potential;

a processor configured to perform one or more operations on the first differential value in response to a target deterioration state to thereby obtain a second differential value;

an operational amplifier configured to acquire a third potential of a first input line at a reference potential side of the external device, wherein the first input line is connected to the first output line in a case where the oxygen sensor is connected to the external device; and an output circuit configured to generate the deterioration signal having as a signal value a fourth potential obtained by superposing the second differential value on the third potential, to thereby output the deterioration signal to a second input line at a sensor potential side of the external device, wherein the second input line is connected to the second output line in a case where the oxygen sensor is connected to the external device.

2. The deterioration signal generation device according to claim 1, wherein the processor configured to perform at least one operation that simulates a predetermined deterioration state selected from the group consisting of:

a gain operation for changing a gain of signal value of the detection signal;

an offset operation for changing a signal value of the detection signal up or down by a fixed amount;

a timing characteristics operation for delaying response of the detection signal to a change in concentration of a specific component in a target gas to be measured; and a response characteristics operation for changing a rate of change of the detection signal in response to a change in concentration of a specific component in a target gas to be measured, to thereby process the first differential value into the second differential value.

* * * * *